(12) United States Patent
Dimick et al.

(10) Patent No.: US 10,175,213 B2
(45) Date of Patent: Jan. 8, 2019

(54) DIRECT IN SITU MONITORING OF ADSORBENT AND CATALYST BEDS

(71) Applicant: INTRAMICRON, INC., Auburn, AL (US)

(72) Inventors: Paul S. Dimick, Waverly, AL (US);
Hongyun Yang, Auburn, AL (US);
Bruce J. Tatarchuk, Auburn, AL (US)

(73) Assignee: INTRAMICRON, INC., Auburn, AL (US)

( * ) Notice: Subject to any disclaimer, the term of this patent is extended or adjusted under 35 U.S.C. 154(b) by 422 days.

(21) Appl. No.: 14/374,606

(22) PCT Filed: Jan. 31, 2013

(86) PCT No.: PCT/US2013/024089
§ 371 (c)(1),
(2) Date: Jul. 25, 2014

(87) PCT Pub. No.: WO2013/116484
PCT Pub. Date: Aug. 8, 2013

(65) Prior Publication Data
US 2014/0370607 A1 Dec. 18, 2014

Related U.S. Application Data

(60) Provisional application No. 61/593,563, filed on Feb. 1, 2012.

(51) Int. Cl.
*G01N 31/10* (2006.01)
*G01N 21/85* (2006.01)
(Continued)

(52) U.S. Cl.
CPC ............. *G01N 31/10* (2013.01); *G01N 21/31* (2013.01); *G01N 21/65* (2013.01); *G01N 21/85* (2013.01); *G01N 2021/8585* (2013.01)

(58) Field of Classification Search
CPC ........................................................ G01N 31/10
See application file for complete search history.

(56) References Cited

U.S. PATENT DOCUMENTS

| | | | |
|---|---|---|---|
| 4,052,470 | A | 10/1977 | Nychka |
| 4,188,309 | A | 2/1980 | Volker |

(Continued)

FOREIGN PATENT DOCUMENTS

WO WO 20110727701 * 6/2011

OTHER PUBLICATIONS

In situ Fourier-transform infrared studies of reaction mechanisms in heterogeneous catalysis Jean-Claude Lavalley, Mohamed Maache, and Jacques Saussey SPIE vol. 1341 Infrared Technology XVI 1990.*

(Continued)

*Primary Examiner* — Krishnan S Menon
*Assistant Examiner* — Dwan A Gerido
(74) *Attorney, Agent, or Firm* — Pabst Patent Group LLP

(57) ABSTRACT

Methods and devices for directly measuring the degree of saturation or degree of deactivation of an adsorbent and/or catalytic bed are described herein. The devices contain an inlet, an outlet, a catalytic and/or adsorbent bed, and optionally a support bed for supporting the catalytic and/or adsorbent bed. The devices further contain one or more structures attached to the reactor that allow for insertion of one or more sensors into the reactor. The sensor is used to spectroscopically interrogate the adsorbent and/or catalyst in situ, providing real-time information regarding adsorbant saturation and/or catalyst deactivation. The devices and methods described herein can be used to determine the saturation degree of adsorbent materials or catalyst beds that are involved in gas-liquid and liquid-liquid heterogeneous systems, such as those used in scrubbing and extraction.

20 Claims, 8 Drawing Sheets

(51) Int. Cl.
G01N 21/31 (2006.01)
G01N 21/65 (2006.01)

(56) References Cited

U.S. PATENT DOCUMENTS

| | | | |
|---|---|---|---|
| 4,294,726 A | 10/1981 | Bozon | |
| 4,908,676 A | 3/1990 | Bedell | |
| 5,192,733 A | 3/1993 | Mainz | |
| 5,712,481 A * | 1/1998 | Welch | G01N 21/359 250/339.12 |
| 6,099,819 A | 8/2000 | Srinivas | |
| 6,716,336 B2 | 4/2004 | Hurland | |
| 6,755,015 B1 | 6/2004 | Manaka | |
| 7,060,233 B1 | 6/2006 | Srinivas | |
| 2008/0038603 A1 | 2/2008 | Lee | |
| 2008/0165361 A1* | 7/2008 | Kauffman | G01N 33/287 356/402 |
| 2011/0014114 A1 | 1/2011 | Schubert | |
| 2012/0309101 A1* | 12/2012 | Horn | G01N 21/8507 436/164 |

OTHER PUBLICATIONS

Copper-Promoted ZnO/SiO2 Regenerable Sorbents for the Room Temperature Removal of H2S from Reformate Gas Streams Priyanka Dhage, Alexander Samokhvalov, Divya Repala, Evert C. Dunin, Michael Bowman, and Bruce J. Tatarchuk Ind. Eng. Chem. Res. 2010, 49, 8388-8396.*

Semiconducting properties of layered cadmium sulphide-based hybrid nanocomposites Zoraya Lopez-Cabana, Clivia Marfa Sotomayor Torres, and Guillermo Gonzalez Nanoscale Research Letters 2011, 6:523.*

Characterization of Diffuse Reflectance FT-IR Spectrometry for Heterogeneous Catalyst Studies Kenneth W. Van Every and Peter R. Griffiths Applied Spectroscopy vol. 45, No. 3, 1991.*

Abatzoglou, et al.,"A review of biogas purification processes", Biofpr Sci., 3:42-71 (2009).

Baiker and Holstein, "Impregnation of alumina with copper chloride modeling of impregnation kinetics and internal copper profites", J Catalysis, 84(1):178-88 (1983).

Behl, "Electrospun nanofibrous metal oxides as regenerable adsorbents for desulfurization of biomass-derived syngas", Ideals, 1-5 2011.

Bukhtiyarova, et al., "XPS study of the silica-supported Fe-containing catalysts for deep or partial H2S oxidation", J Mole Catalysis, 158:251-5 (2000).

Campos-Martin, et al., "Oxidative processes of desulfurization of liquid fuels", Instituto de Catalisis y Petroleoquimica, pp. 1-33 (2010).

Curtis, "Molybdenum/cobalt/sulfur clusters: Models and precursors for hydrodesulfurization (HDS) catalysts", Applied Organometallic Chem., 6:429-36 (1992).

Fayos, et al., "Study of supported copper chloride catalysts by electron paramagnetic resonance and X-ray diffraction", J Catalysis, 31(2):257-63 (1973).

Hutchings, et al., "Influence of chlorine poisoning of copper/alumina catalyst on the selective hydrogenation of crotonaldehyde", Catalysis Lttrs., 23(127-33 (1994).

International Preliminary Report of Patentability for PCT/US2013/024089 dated Apr. 8, 2014.

International Search Report and Written Opinion for PCT/US2013/024089 dated Apr. 23, 2013.

Lavalley, et al., "In situ frontier-transform infrared studies of reaction mechanisms in heterogeneous catalysis", Infrared Tech XVI, 1341:244-55 (1990).

Leofanti, et al., "Alumina-supported copper chloride 1. Characterizsation of freshly prepared catalyst", J Catalysis, 189(1):91-104 (2000a).

Leofanti, et al., "Alumina-supported copper chloride 2. Effects of aging and thermal treatments", J Catalysis, 188:105-16 (2000b).

Muddada, et al., "Quantification of copp[er phases, their reducibility and dispersion in doped-CuCl2/Al2O3 catalysts for ethylene oxychlorination", Dalton Trans, 39(36):8437-49 (2010).

Salavati-Niasari, et al., "Oxidation of cyclohexane with tert-butylhydroperoxide and hydrogen peroxide catalyzed by alumina-supported manganese(II) complexes", J Mole Catalysis, 186(101-7 (2002).

Yoo, et al., "Advanced De-Sox catalyst: Mixed solid solution spinels with cerium oxide", Applied Catalysis 3(29):169-89 (1992).

Zhang, et al., "Catalytic effects of metal oxides on the decomposition of potassium perchlorate", Thermochinica Acta, 278:119-27 (1996).

* cited by examiner

DIRECT IN SITU MONITORING OF ADSORBENT AND CATALYST BEDS

CROSS-REFERENCE TO RELATED APPLICATIONS

This application is an application under 35 U.S.C. § 371 of copending PCT application No. PCT/US2013/024089, filed Jan. 31, 2013, which claims benefit of U.S. Provisional Application No. 61/593,563, filed Feb. 1, 2012.

FIELD OF THE INVENTION

The present invention is in the field of methods to determine the degree of saturation of adsorbents or degree of deactivation of catalyst beds by monitoring the changes in the optical properties of a solid surface in gas-solid and liquid-solid heterogeneous processes.

BACKGROUND OF THE INVENTION

Heterogeneous reactions are widely employed in both industry applications and lab scale experiments. Gas-solid, liquid-solid, and gas-liquid reactions are the most common examples of heterogeneous reactions. The physical properties of solid surface, liquid streams and gas streams change as the reaction(s) proceed. If one of those physical properties can be measured as a function of time, then the degree of saturation or available capacity can be estimated. Such estimates can be used to determine when the solid surface needs to be replaced in order to optimize the efficiency and efficacy of the heterogeneous reaction.

Significant research and development efforts have been made to develop a means for monitoring adsorbent capacity, especially for desulfurization systems for fuel cell applications. The majority of these efforts involve measuring changes in the sulfur concentration in a fuel stream upon passage through a sorbent bed. For example, U.S. Patent Application Publication No. 2008/0038603 to Lee et al. describes a method to determine sulfur concentration by measuring changes in electrical, physical, or chemical properties during desulfurization. The methods described in Lee require at least two sensors, one at the inlet of the sorbent bed and one at the outlet of the sorbent bed, which are used to measure the difference in sulfur concentration upon passage through the sorbent bed. The difference in sulfur concentration is then used to estimate the degree of saturation of the adsorbent material U.S. Pat. No. 6,716,336 to Hurland describes a sulfur sensor to determine sulfur concentration of a liquid stream. The methods involve measuring the change in potential between a working electrode and a reference electrode separated by a silver ion conductor. Sulfur bonds readily with silver ions, therefore, the potential changes with sulfur concentration in the stream.

Both of the methods described above use sulfur concentration as a means for estimating the remaining adsorptive capacity of an adsorbent material. In the case of Hurland, streams containing low sulfur concentrations may produce potential changes that are undetectable by the method described therein.

Changes in optical properties have been also been used for catalyst characterization to determine adsorbate concentration. For example, commercial in-line $H_2S$ detectors can measure $H_2S$ concentration by measuring the color changes of lead acid paper in process stream containing $H_2S$. Although it has stringent requirements for relative humidity, temperature and exposure time for accurate measurement, this method provides an economical way to measure sulfur concentration. In order to continuously measure $H_2S$ concentration, a roll of lead-acid tape is continuously fed to the detecting unit which increases cost of the this method and requires disposal of the lead-acid tape.

U.S. Pat. No. 6,755,015 to Manaka describes methods for measuring $NO_x$ adsorption. For example, Manaka describes measuring chemical species concentration before and after the adsorbent bed. If the concentration or signal captured downstream of the bed is higher than a critical value, then the adsorbent bed is considered exhausted. Alternatively, $NO_x$ removal rate can be determined based on concentration or signal captured both upstream and downstream of the adsorbent bed. If the $NO_x$ removal rate is blow a critical value, then the bed is also considered exhausted.

None of the prior art discussed above directly measures the degree of saturation of the adsorbent material or catalyst bed itself; rather, the prior art methods involve measuring sulfur concentration and using that measurement to estimate the remaining adsorptive or catalytic capacity. While these approaches may be effective with a constant adsorbate concentration or known adsorbent concentration profile in the gas stream, these methods may have limitations with significant changes in concentration, i.e., high concentration variations. For example, if the adsorbate (sulfur or $NO_x$) concentration suddenly increases, the outlet concentration of the chemical species may increase to above the critical breakthrough concentration. According to Manaka's method, capacity depletion will be detected. Similarly, if the inlet concentration has a sudden drop in its concentration, the downstream concentration and calculated adsorbate removal rate will drop too and another capacity depletion signal will be given. In order to determine false signals, the relationship of the adsorbate concentration and degree of saturation must be established for various scenarios. Moreover, the methods described above require at least two sensors, at the inlet and outlet or before and after the bed, in order calculate sulfur or $NO_x$ concentration. Systems with two sensors are more prone to reliability issues than a single sensor system.

In view of the limitations discussed above, there exists a need for a method of determining adsorptive capacity or catalyst deactivation that does not require two sensors and the accuracy of which is not dependent on measuring the concentration of one or more contaminant species.

Therefore, it is an object of the invention to provide methods for determining adsorptive capacity or catalyst deactivation that does not require two sensors.

It is also an object of the invention to provide methods for determining adsorptive capacity or catalyst deactivation the accuracy of which is independent of the concentration of one or more contaminant species.

SUMMARY OF THE INVENTION

Methods and devices for directly measuring the degree of saturation or degree of deactivation of an adsorbent and/or catalytic bed are described herein. Unlike the prior art, the methods described here do not rely on measuring the concentration of a contaminant and/or reactive species and correlating the differences in concentration to the degree of saturation or deactivation. Such methods require the use of at least two sensors, at the inlet and outlet of the reactor or before and after the bed or beds to be monitored. In contrast, the methods described herein can be conducted using a single sensor inserted into the bed. Multiple sensors can be used to develop a map of the degree of saturation and/or deactivation along the bed. The methods described herein measure one or more changes in the adsorbent and/or catalytic bed itself.

The device contains an inlet, an outlet, a catalytic and/or adsorbent bed, and optionally a support bed for supporting the catalytic and/or adsorbent bed. The device further contains a structure attached to the reactor that allows for insertion of a probe or sensor into the reactor. Suitable structures include compression fittings, weldments, flanges, and O-ring sealed fittings, such as an Ultra-Torr Fitting. The structure should form a gas tight seal once the probe or sensor is inserted. In commercial operations the device can contain additional components, such as additional beds, sensors, and combinations thereof as required for a given application.

The methods described herein can be used to changes in a variety of properties of the adsorbent or catalyst, such as optical properties, density, magnetic properties, temperature, etc.

In one embodiment, the methods described herein are used to measure changes in the optical properties of the bed. In a particular embodiment, the sensor includes a means for delivering electromagnetic radiation to and from the bed surface, such as fiber optic wire. The sensor is connected to an electromagnetic radiation source, such as a UV-Vis light source, an infra red light source, or combinations thereof. The sensor can deliver monochromatic radiation or polychromatic radiation depending on the type of characterization to be performed. The sensor is also connected to a spectrophotometer for detecting/collecting the radiation reflected from the surface of the bed and analyzing/processing the data. The characterization can be performed using the raw data or processed data, such as absorbance, transmittance, or reflectance.

In some embodiments, the methods and devices described herein can be used to monitor beds use for desulfurization. Sulfur containing gas (e.g. $H_2S$ in $H_2$) passes through an adsorbent bed of zinc oxide (ZnO) and $H_2S$ is captured by ZnO according to the following reaction:

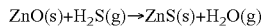

$$ZnO(s)+H_2S(g) \rightarrow ZnS(s)+H_2O(g)$$

As the reaction continues, the ZnO surface is gradually replaced with zinc sulfide (ZnS). The color of the surface changes from bright yellow to dark beige. Similarly, copper oxide doped ZnO sorbent changed its color from light blue to dark green. These color changes can be detected spectroscopically to indicate it is time for the bed to be replaced/regenerated.

Another example is catalyst deactivation. In some processes of catalytic reforming, soot formation is a major cause of catalyst deactivation. Carbon precipitation on the catalyst surface changes the catalyst surface to black and the catalyst gradually loses its activity.

Other applications include measuring changes in one or more properties of the adsorbment material or catalyst bed due to adsorption of other materials, such as water (e.g., moisture); acids, such as hydrochloric acid (HCl), sulfuric acid, and nitric acid; nitrogen containing compounds, such as ammonia and $NO_x$; carbon containing compounds, such as carbon dioxide, carbon monoxide, aliphatic hydrocarbons, and polyaromatic hydrocarbons.

If the adsorbent and catalyst employed is a liquid, then the light transmitted from the stream is detected. The color changes detected by these detectors will be collected in form of a signal as a function of time. The signal or the changes in signal overtime indicates the degree of capacity depletion or catalyst deactivation and provides an estimate of when the adsorbent and/or catalyst should be replaced. With this information, the processes can be safely operated at high adsorbent/catalyst utilization and reduced operational costs.

The methods described herein allow the degree of saturation of the adsorbent material or catalyst bed to be determined even in in the presence of competing species that can induce a change in the surface chemistry of the adsorbent material or catalyst bed. Exemplary competing species include, but are not limited to, carbon dioxide, carbon monoxide, moisture, nitrogen, or combinations thereof.

DETAILED DESCRIPTION OF THE INVENTION

I. Definitions

Figure 1:
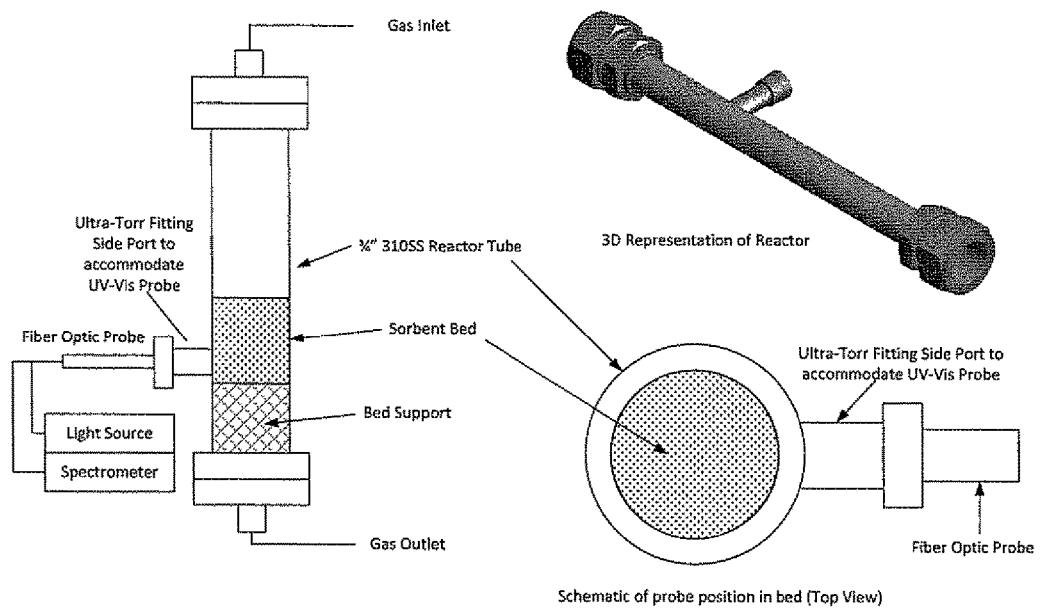
FIG. 1 is a schematic of a reactor containing a fiber optic sensor.

"Absorbance", used herein, generally means the logarithm of the intensity of the electromagnetic radiation ($I_0$) reflected from or transmitted through a catalyst or sorbent that may be interacting with a fluid phase at some time divided by the intensity of the electromagnetic radiation reflected (I) from or transmitted through a catalyst or sorbent that may be interacting with a fluid phase at another time (t).

"Transmission", used herein, generally means the logarithm of the intensity of the electromagnetic radiation (I) reflected from or transmitted through a catalyst or sorbent that may be interacting with a fluid phase at some time divided by the intensity of the electromagnetic radiation ($I_0$) reflected from or transmitted through a catalyst or sorbent that may be interacting with a fluid phase at another time.

"Reflectance", as used herein, refers to the intensity of the light reflected from or transmitted through a catalyst or sorbent.

"Color", as used herein, refers to the frequency or wavenumber of the light sources or electromagnetic fields.

"Breakthrough", as used herein, generally means a process in which the sulfur species or other contaminant species advance in and gradually penetrate through a bed made of materials than can capture those species.

"Oxidative sulfur removal", as used herein, generally means the oxidation of sulfur-containing compounds to elemental sulfur. In particular embodiment, sulfur-containing compounds are oxidized to elemental sulfur with little or no generation of sulfur dioxide. The elemental sulfur can be condensed as a liquid or a solid.

"Catalyst", as used herein, refers to one or more substrates in combination with one or more compounds or materials that have catalytic activity.

"Substrate", as used herein, refers to one or more support materials that may be non-reactive when contacted by sulfur containing fuel streams and oxygen-containing gases. Some reaction of the substrate material can be tolerated provided it does not adversely affect the oxidative sulfur removal reaction.

"Reactive metal salts", as used herein, generally refers to metal salts responsible for the catalytic activity with sulfur-containing species found in the fuel stream.

"Physically absorbed", as used herein, generally means that the one or more reactive metal salts are physically associated with (e.g., physically adsorbed to), not chemically bound to, the one or more substrates.

"Oxygen sponge", as used herein, refers to a compound or compounds that facilitate oxygen adsorption, transport, and/or reaction.

"Impregnating", as used herein, generally means the process of placing the reactive metal salts, oxygen sponges, and/or their precursors on the supports. In some embodiments, this is done by allowing the substrate to interact with these components, typically in a solution. The impregnation step can be followed by thermal treatments to generate the catalyst in its final form.

"Fluid", as used herein, generally means a substance that has no fixed shape and yields easily to external pressure, such as a liquid and/or gas. Fluid fuel stream can be in the form of a liquid and/or gas.

"Gaseous fuel stream", as used herein, generally refers to a fuel stream that is in the form of a gas.

"High sulfur content", as used herein, generally means fuel streams, such as gaseous fuel streams, which contain sulfur-containing compounds in an amount from at least about 300 ppm to about 40,000 ppm.

II. Methods for Direct in situ Monitoring of Adsorbent and Catalyst Beds

Methods for the direct in situ monitoring of adsorptive capacity of an adsorption bed or catalyst deactivation in a catalyst bed are described herein. The methods involve direct measurement of a change in one or more properties of the adsorptive or catalytic material itself and therefore can be measured effectively with a single sensor. However, multiple sensors can be used at different locations in the bed in order to map the degree of saturation or deactivation at different locations of in the bed. The method does not rely on measurement of an indicator layer within in the bed.

The methods described herein allow the degree of saturation of the adsorbent material or catalyst bed to be determined even in in the presence of competing species that can induce a change in the surface chemistry of the adsorbent material or catalyst bed. Exemplary competing species include, but are not limited to, carbon dioxide, carbon monoxide, moisture, nitrogen, or combinations thereof.

The methods described herein generally measure the changes in optical properties of the bed material. However, changes in other properties can be measured, such as changes in density, magnetic properties, temperature, etc.

The change in optical properties can be determined from the raw data or from processed data, such as absorbance, transmission, or reflectance. Changes in optical properties may be the most straightforward to measure and may most accurately reflect direct changes to the absorbent, such as those that occur during sulfidation. The methods described herein can be used to determine the saturation degree of adsorbent materials or catalyst beds that are involved in gas-liquid and liquid-liquid heterogeneous systems such as scrubbing and extraction. The method can be employed for adsorption processes, catalytic processes with catalyst deactivation, and/or liquid scrubbing processes.

A. Apparatus for Direct in situ Monitoring of Adsorbent or Catalyst Bed

The methods described herein involve an apparatus or device to directly monitor the adsorbent or catalyst bed itself. The apparatus or device generally includes a reactor and a probe or sensor. The reactor, which can be any size and shape, such as a tube, contains the adsorbent or catalyst bed. The reactor can also contain a bed support for supporting the adsorbent or catalyst bed.

The reactor typically contains a fitting, such as a side port, in order to accommodate the probe/sensor. Examples include compression fittings, weldments, flanges, and O-ring sealed fittings such as an Ultra-Torr Fitting. The Ultra-Torr Fitting should provide a gas-tight seal between the reactor and sensor/probe. For those embodiments where changes in optical properties are measured, the probe or sensor is connected to an electromagnetic radiation source, a means for delivering the electromagnetic radiation to and from the bed, and a spectrophotometer for detecting/collecting and processing the electromagnetic radiation reflected from the bed. A schematic of a representative apparatus, including the sensor and the reactor, is shown in FIG. 1.

The probe or sensor is connected a source of electromagnetic radiation. The source can be programmable, that is the source can emit a single wavelength of radiation or multiple wavelengths or a range of wavelengths or multiple ranges of wavelengths. Suitable sources include sources that generate ultraviolet and visible light (UV-Vis spectroscopy) and infrared light (IR spectroscopy). For example, the source can be a light emitting diode, a photodiode, or a laser. The source can further contain a monochrometer or grate to selective transmit one or more wavelengths of light.

Raman spectroscopy can also be used to analyze the bed material. Raman spectroscopy is a spectroscopic technique used to study vibrational, rotational, and other low-frequency modes in a system. It relies on inelastic scattering, or Raman scattering, of monochromatic light, usually from a laser in the visible, near infrared, or near ultraviolet range. The laser light interacts with molecular vibrations, phonons or other excitations in the system, resulting in the energy of the laser photons being shifted up or down. The shift in energy gives information about the vibrational modes in the system. Infrared spectroscopy yields similar, but complementary, information.

The probe or sensor also contains a means for delivering the electromagnetic radiation to and from the bed material. Suitable means include fiber optic wire or cable, through the atmosphere, and/or one or more lenses.

The sensor or probe is connected to a device for detecting/collect the electromagnetic radiation reflected from the surface of the adsorbent or catalytic material, such as a spectrophotometer for. Suitable spectrophotometers include UV-Vis spectrophotometers, IR spectrophotometers, Raman spectrophotometers, and combinations thereof.

Figure 2A:
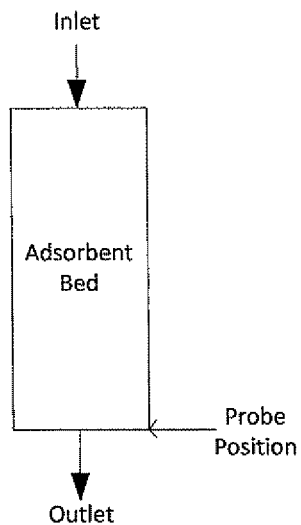
FIG. 2A is a schematic showing placement of the probe at the bottom of the bed.
Figure 2B:
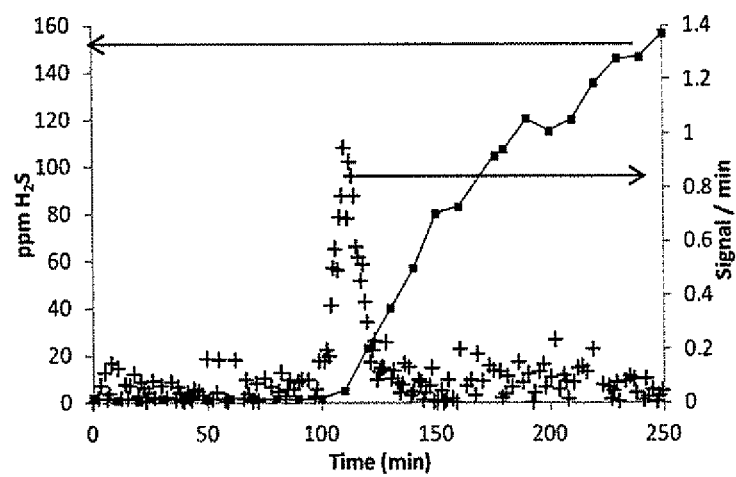
FIG. 2B is a graph showing $H_2S$ breakthrough curve and detector response with the probe at the bottom of the bed.
Figure 3A:
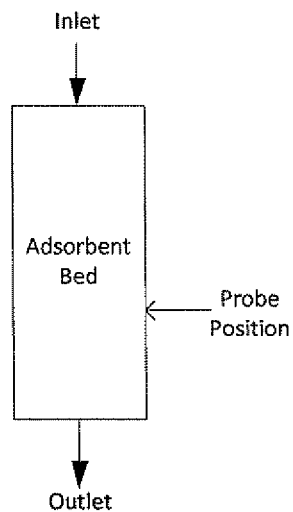
FIG. 3A is a schematic showing placement of the probe ⅔ down the length of the bed.
Figure 3B:
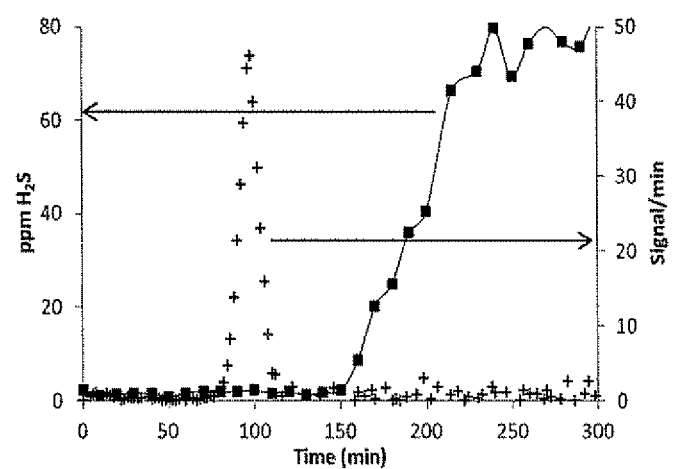
FIG. 3B is a graph showing $H_2S$ breakthrough curve and detector response with the probe placed ⅔ of the way down the bed.

The reactor can be fitted with a single sensor at any location along the bed. Examples of different locations of the sensor are shown in FIGS. 2A and 3A. Spectra showing $H_2S$ breakthrough are shown in FIGS. 2B and 3B. Alternatively, multiple sensors can be inserted at various locations along the bed so that one can determine the degree of saturation or deactivation at different points along the bed The exemplary apparatus described above can be used to evaluate the efficacy of monitoring the bed on a bench top scale. On a commercial scale, the size of the reactor and the bed can be increased to accommodate the desired application.

Other components may be added to the apparatus, either as part of the apparatus or in addition to the apparatus depending on the application. For example, for desulfurization processes of gaseous fuel streams, the apparatus can additionally include a condenser to condense the liquid sulfur generated from the conversion of sulfur-containing compounds to elemental sulfur by the catalyst bed. Gaseous elemental sulfur can be condensed to a liquid by lowering the temperature of the fuel stream, for example to a temperature below 250° C., preferably below 180° C. by passing it through the condenser. Liquid sulfur can be removed from gaseous fuel streams using vapor-liquid separators. The liquid sulfur can be further cooled and condensed to form solid elemental sulfur which can be removed by particle filtration.

The apparatus can also contain a sorbent bed to move remaining sulfur-containing compounds after the fuel stream contacts the catalyst bed. One or more sensors can be placed along the catalyst bed and/or adsorbent bed to monitor the catalytic deactivation and/or adsorptive capacity of the materials i. Adsorbent and Catalytic Materials The bed contains one or more adsorbent materials, catalytic materials, or combinations thereof. In some embodiments, the materials can be chosen to selectively adsorb or react with one or more contaminants, such as those found in fluid fuel streams. Exemplary contaminants include, but are not limited to, sulfur-containing compounds, such as hydrogen sulfide, mercaptans, thiols, $CS_2$, R—S—R, COS, $SO_2$, and $SO_3$; nitrogen containing compounds, such as $NO_x$; ammonia; arsenides; halides; and combinations thereof.

Suitable bed materials include adsorbents and catalysts known in the art for removing contaminants such as hydrogen sulfide, mercaptans, COS, and $NO_x$. Exemplary materials include, but are not limited to, metal oxides and mixed metal oxides, such as zinc oxide (ZnO), supported zinc oxide, iron oxides (FeO, $Fe_2O_3$), supported iron oxides, Copper Oxides ($Cu_2O$ and CuO), supported copper oxides, metal hydroxides, iron chelates, iron salts, activated carbons, impregnated activated carbons, zeolites, and combinations thereof.

In some embodiments, the catalyst is an oxidative sulfur removal (OSR) catalyst containing one or more reactive metal salts impregnated or adsorbed onto the surface of a substrate. The catalysts compositions can be used to selectively oxidize sulfur-containing compounds, such as $H_2S$, to elemental sulfur according to Equation 1.

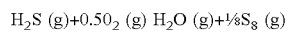

$$H_2S\ (g) + 0.5O_2\ (g) \rightarrow H_2O\ (g) + \tfrac{1}{8}S_8\ (g)$$

The catalyst described herein can be used to treat a variety of fuel streams, particularly gaseous fuel streams, such as biogas, frac gas, gasified biomass, and gasified coal/bitumen, including those have high sulfur content.

Suitable substrates include activated carbon, metal or metalloid oxides, and combinations thereof. In some embodiments, the substrate is two or more metal or metalloid oxides, herein referred to as mixed metal oxides. Suitable metals include transition metals such as titanium, and metalloids, such as silicon and aluminum. Exemplary metal and metalloid oxides include, but are not limited to, aluminum oxide ($Al_2O_3$), titanium dioxide ($TiO_2$), silicon dioxide ($SiO_2$), ceria, and combinations thereof. The one or more substrate materials are generally present in an amount from about 80% to about 99% by weight of the catalyst, preferably from about 80% to about 95% by weight of the catalyst, more preferably from about 90% to about 95% by weight of the composition.

In order to load sufficient amounts of the metal salts on the substrates, substrates with large pore volume are preferred. Typical pore volume is around 0.2-1.2 cc/g of support. Typical medium pore diameter is in the range of 10-200 Å. High surface area helps to facilitate the oxidation reaction. Typical surface area is in the range of 40-600 $m^2/g$ of support.

Particle size is typically less than 3 mm due to slow mass transfer of sulfur vapor inside the catalyst particles. Minimal particle size is selected such that significant pressures drops are avoided. Accordingly, the particle size is typically in the range of 14-20 mesh (0.8-1.4 mm).

The one or more reactive metal salts are primarily responsible for the catalytic activity of the catalyst. In some embodiments, the metal salts are multivariable metals having variable valence or oxidation states and having catalytic activity with sulfur compounds in the fuel stream. Examples of these classes of salts include, but are not limited to, chlorides of transition metals having multiple oxidation states, sulfates of transition metals having multiple oxidation states, and combinations thereof. Examples of species of these salts include, but are not limited to, CuCl, $MnCl_2$, $MnSO_4$, $FeCl_2$, $FeCl_3$, $NiCl_2$, $NiSO_4$, and $FeSO_4/Fe_2(SO_4)_3$.

For the reactive metal salts described herein, it is preferred that (1) the metal ions are in the lowest or a lower oxidation state; (2) the metal ions can be oxidized to the next higher oxidation state by oxygen in the temperature range of 100-300° C.; (3) the metal ions at higher oxidation states can oxidize $H_2S$ to elemental sulfur; (4) the cations will not be oxidized by the metal ions at the next higher oxidization state; and (5) the salts must be thermally and chemically stable for various operation conditions.

In other embodiments, the reactive metal salts are salts of alkaline and alkali earth metals, particularly those metals after the third row in the periodic table, such as bromide and iodide salts. Examples include, but are not limited to, KI, $CaI_2$, and combinations thereof. For salts such as $MnI_2$ and $MnBr_2$, Mn cannot be oxidized to its highest oxidization state without oxidizing $I^-$ and perhaps $Br^-$. As a result, elemental iodine and bromine are generated as intermediates. These intermediates can oxidize $H_2S$ and generate elemental sulfur.

The reactive metals salts can be used alone or in combinations of one or more of the salts described above. The one or more reactive metal salts are present in an amount from about 1% to about 20% by weight of the catalyst, preferably from about 1% to about 10% by weight of the catalyst, more preferably from about 5% to about 10% by weight of the catalyst. In some embodiments, the amount of the one or more reactive salts is about 7% by weight of the catalyst.

The catalyst can also contain one or more compounds that function as an oxygen sponge under the reaction conditions for oxidative sulfur removal. In some embodiments, the oxygen sponge is one or more metal oxides. Examples of suitable metal oxides include, but are not limited to, lanthanide oxides, such as cerium oxide and alkaline earth oxides, such as magnesium oxide.

III. Applications

The methods and devices described herein can be used to directly monitor catalytic and/or adsorbent beds used in a variety of commercially important applications. For example, the methods and devices described herein can be used to monitor catalytic and/or adsorptive beds used to remove a variety of undesirable compounds or contaminants, such as sulfur-containing compounds and other contaminants from fuel streams prior to the fuel source being fed into a fuel cell. Exemplary fuel streams include land fill gases, natural gas from natural gas wells, flammable gases from oil wells, flammable gases from tar sands, syngas, and flare gas (methane). Similar examples include liquid phase desulfurization by sorbent materials (e.g. Cu(I)—Y zeolite, Ag/TiO2, etc.) and adsorption processes to remove ammonia, arsenides, halogenated species in various industries.

This method can also be applied to catalytic processes. Most catalysts will lose their activity due to carbon formation on the surface of catalyst, catalyst poisoning (by e.g. sulfur species or halogens), phase changes of catalyst or catalyst supports, etc. These changes can also be measured by the method described herein.

Other applications include measuring changes in one or more properties, such as optical properties, of the adsorbment material or catalyst bed due to adsorption of other materials, such as water (e.g., moisture); acids, such as hydrochloric acid (HCl), sulfuric acid, and nitric acid; nitrogen containing compounds, such as ammonia and $NO_x$; carbon containing compounds, such as carbon dioxide, carbon monoxide, aliphatic hydrocarbons, and polyaromatic hydrocarbons.

As discussed below, studies to predict breakthrough in a $CuZn/SiO_2$ sorbent bed were evaluated by conducting a simultaneous breakthrough and spectroscopy study on 15 wt % CuZn supported on $SiO_2$ with a feed of 870 ppm $H_2S$ in $H_2$ at a face velocity of 10 cm/s and a residence time of 1 second at room temperature. The bed length was 10 cm and the probe was positioned in the last 0.6 cm of the bed. A spectrum of the fresh sorbent was used as the reference spectrum for the system when calculating absorbance. Following sulfidation, a broad peak was observed at between 300 and 550 nm having a maximum at 350 nm. The appearance of this peak can be attributed to the formation of ZnS and CuS species on the sorbent surface.

Several data processing methods for sensing the saturation of the sorbent were evaluated. The first method was to compare the integrated area of the absorbance spectra from 300 nm to 500 nm as a function of time. The 300 nm to 500 nm range was selected because it is the region of the spectrum where most of the changes in peak area resulting from sulfidation occur. Comparing the integrated area as a function of time to the $H_2S$ breakthrough curve for the test conducted with a feed of 870 ppm $H_2S$ in $H_2$, showed that the UV-Vis signal was a good indicator of breakthrough. The UV-Vis signal had a faster response (higher slope) than the $H_2S$ breakthrough profile.

The second signal processing method evaluated was examining the absorbance at 400 nm as a function of time. This wavelength was selected because it is approximately in the center of the peak resulting from sulfidation. Similar to the integrated peak area method, using the spectral value at a given wavelength also was a good indicator of breakthrough. As expected because of the result from the integrated area method, this method also has a stronger response (higher slope) than the $H_2S$ breakthrough profile.

Since both signal processing methods described above mimic the $H_2S$ breakthrough curve for the system, it is necessary to examine a signal processing method that will indicate when the measured portion of the bed has reached a certain saturation level. By examining the derivative of the integrated area or value of the spectrum at a given wavelength (400 nm), the midpoint (t50) of the signal curve to be identified can be determined by watching for the maximum of the derivative as a function of time. The maximum of the integrated area time derivative occurred when the bed reached approximately 25% of its capacity.

The derivative of the integrated spectral area was selected as the method that would provide the best method to sense the point when the bed has become saturated because it results in a single peak that can be detected to indicate that the bed is reaching the end of its useful life.

Experiments were also conducted at significantly lower sulfur concentrations to evaluate the sensitivity of the technique. Experiments at a concentration of 162 ppm $H_2S$ in $H_2$ were conducted. As with the test conducted at 870 ppm, the UV-Vis sensing method was able to predict $H_2S$ breakthrough as indicated by the maximum of the spectral area derivative at the breakthrough point. A similar result was obtained for the test conducted with an inlet $H_2S$ concentration of 63 ppm.

The ability to monitor the bed in the presence of competing species/contaminants was also evaluated. The presence of 20% $CO_2$ and 20% $CO_2$ at 50% relative humidity did not have an impact on the ability of the derivative of the integrated spectrum area to predict breakthrough. For both of these tests spectral changes significant enough to impact the sensing method were not observed. The presence of $CO_2$ in the feed resulted in the formation of a small peak centered below 300 nm. The magnitude of this peak was significantly less than the peak resulting from the sulfidation of the sorbent.

The final test to screen whether the presence of other components impact the ability of the method to sense breakthrough was conducted with an atmosphere containing 250 ppm $H_2S$, 20% $CO_2$, 20% CO, 20% $N_2$, and a balance of $H_2$. The maximum of the derivative for the integrated UV-Vis Signal was observed 30 minutes before breakthrough occurred.

EXAMPLES

Materials and Methods

An experimental setup for testing the capability of using UV-Vis DRS to determine breakthrough for a Cu—Zn/$SiO_2$ adsorbent was conducted. A 16 mm ID stainless steel tube was constructed with a ¼ inch side port for the sensing probe. The sensing probe was inserted into the side port and a bed of adsorbent (Mass=2 g, V=4 $cm^3$) was packed in the tube so that the probe was positioned at the bottom of the bed. A feed stream with the desired concentration of $H_2S$ in $H_2$ was passed through the adsorbent bed at a face velocity of 10 cm/s. The signal from the probe was collected and processed at the same time the outlet concentration from the adsorbent bed was measured with a gas chromatograph equipped with a pulsed flame photometric detector.

The Ultra-Torr side port welded to the reactor allows a gas-tight seal to be made when the probe is inserted into the bed (see FIG. 1). This type of fitting was selected because it relies on an o-ring seal allowing the probe to be used without causing any damage to the outer portion of the probe. This flexibility allows the probe position to easily be adjusted to determine the optimal sensor orientation.

Example 1

Predicting Breakthrough on CuZn Supported on $SiO_2$

The ability to use in situ UV-Vis spectroscopy to predict breakthrough in a CuZn/$SiO_2$ sorbent bed was first evaluated by conducting a simultaneous breakthrough and spectroscopy study on 15 wt % CuZn supported on $SiO_2$ with a feed of 870 ppm $H_2S$ in $H_2$ at a face velocity of 10 cm/s and a residence time of 1 second at room temperature. Under these conditions, the bed length was 10 cm and the probe was positioned in the last 0.6 cm of the bed. The spectrometer acquisition conditions were optimized for the experimental setup and spectra were collected every 2 minutes over the course of the breakthrough test. A spectrum of the fresh sorbent was used as the reference spectrum for the system when calculating absorbance.

Figure 4:
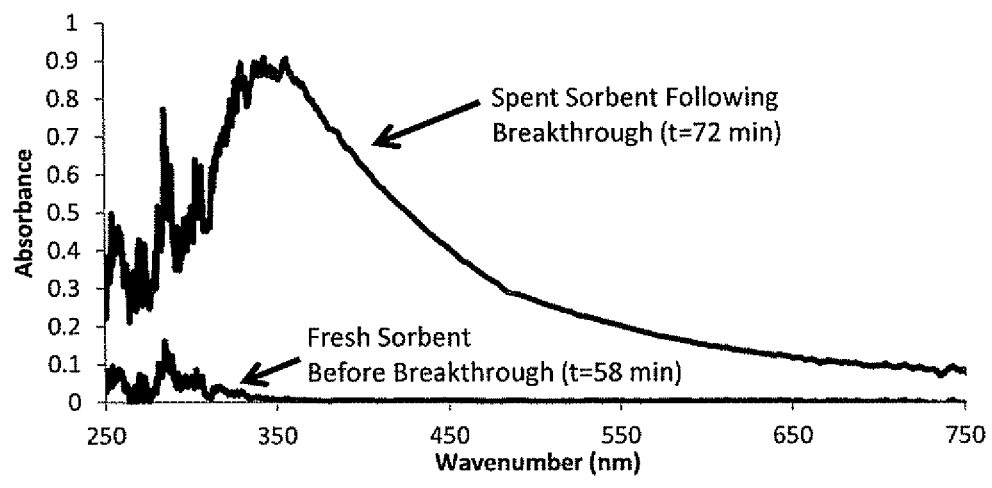
FIG. 4 is an absorption spectrum from fresh (t=58 min) and spent (t=72 min) Cu—Zn/$SiO_2$ sorbent during a breakthrough study with 870 ppm $H_2S$ in $H_2$ at a face velocity of 10 cm/s and a residence time of 1 second.

Spectra of the CuZn/$SiO_2$ sorbent before breakthrough (t=58 min, FIG. 4 maroon line) and after saturation (t=72 min, FIG. 4 blue line) are presented in FIG. 4. The small peaks present in the spectra of the fresh sorbent between 250 nm and 300 nm may have structural importance; however, they cannot be identified because there is a significant amount of noise due to low signal in this range. The low signal in this range is directly related to the light source and the spectrometer that is being used for the study. Following sulfidation, a broad peak was observed at between 300 and 550 nm having a maximum at 350 nm. The appearance of this peak can be attributed to the formation of ZnS and CuS species on the sorbent surface. Several band assignments for relative peaks from the literature have been included in FIG. 4.

Figure 5:
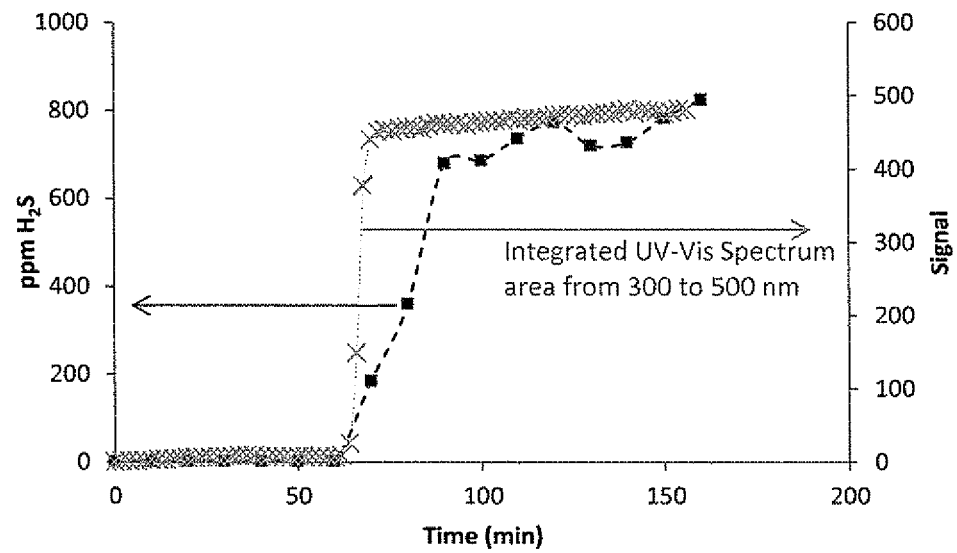
FIG. 5 is a spectrum showing $H_2S$ breakthrough and integrated UV-Vis spectrum area (from 300 nm to 500 nm) for an adsorption test with a feed of 870 ppm $H_2S$ in $H_2$ at a face velocity of 10 cm/s and a residence time of 1 second.

Following evaluation of the spectrum presented in FIG. 4, several data processing methods for sensing the saturation of the sorbent. The first method was to compare the integrated area of the absorbance spectra from 300 nm to 500 nm as a function of time (FIG. 5). The 300 nm to 500 nm range was selected because it is the region of the spectrum where most of the change in peak area resulting from sulfidation occurs. The lower limit of the integration window was partially selected because at wavelengths less than 300 nm, the signal to noise ratio was too low for sufficient sensing to occur. Comparing the integrated area as a function of time to the $H_2S$ breakthrough curve for the test conducted with a feed of 870 ppm $H_2S$ in $H_2$, showed that the UV-Vis signal was a good indicator of breakthrough. The UV-Vis signal had a faster response (higher slope) than the $H_2S$ breakthrough profile.

Figure 6:
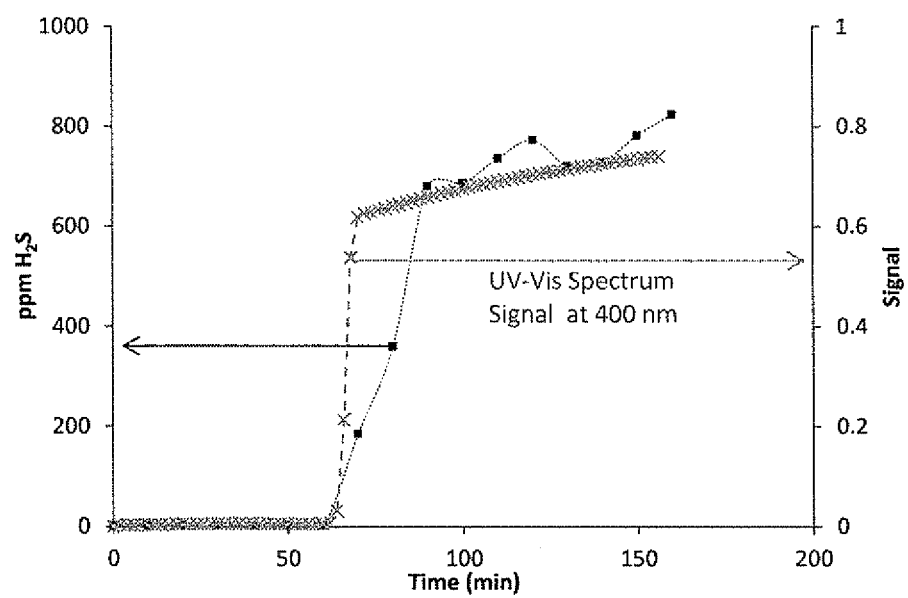
FIG. 6 is a spectrum showing $H_2S$ breakthrough and integrated UV-Vis spectral intensity at 400 nm for an adsorption test with a feed of 870 ppm $H_2S$ in $H_2$ at a face velocity of 10 cm/s and a residence time of 1 second.

The second signal processing method evaluated was examining the absorbance at 400 nm as a function of time. This wavelength was selected because it is approximately in the center of the peak resulting from sulfidation. While the maximum peak intensity does not occur at this wavelength, choosing the central wavelength of this peak minimizes the impact of other spectral features that are present at a lower or higher wavelength. Based on an analysis of the collected spectra, it is possible that there are some structural features that have peaks in the range of 200 nm-300 nm due to the formation of carbonate species (data not shown). If these peaks have significant intensity and a single wavelength close to these peaks is used for analysis it could impact the sensitivity and accuracy of the measurement method. The results are shown in FIG. 6. Similar to the integrated peak area method, using the spectral value at a given wavelength also was a good indicator of breakthrough. As expected because of the result from the integrated area method, this method also has a stronger response (higher slope) than the $H_2S$ breakthrough profile.

Figure 7:
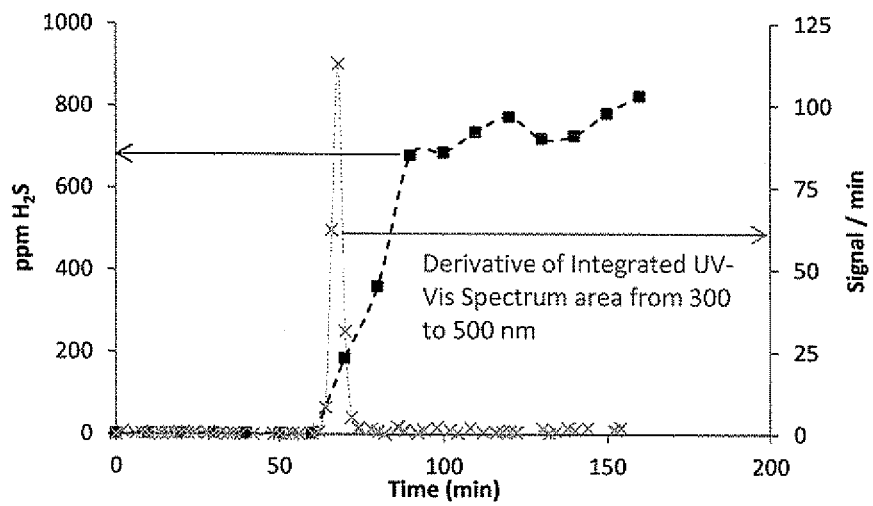
FIG. 7 is a spectrum showing $H_2S$ breakthrough and derivative of integrated UV-Vis spectrum area from 300 nm to 500 nm versus time for an adsorption test with a feed of 870 ppm $H_2S$ in $H_2$ at a face velocity of 10 cm/s and a residence time of 1 second.

Since both signal processing methods mimic the $H_2S$ breakthrough curve for the system, it is necessary to examine a signal processing method that will indicate when the measured portion of the bed has reached a certain saturation level. By examining the derivative of the integrated area or value of the spectrum at a given wavelength (400 nm), the midpoint (t50) of the signal curve to be identified can be determined by watching for the maximum of the derivative as a function of time. An example of the time derivative of the integrated area compared with the $H_2S$ breakthrough is presented in FIG. 7. The maximum of the integrated area time derivative occurred when the bed reached approximately 25% of its capacity.

The derivative of the integrated spectral area was selected as the method that would provide the best method to sense the point when the bed has become saturated because it results in a single peak that can be detected to indicate that the bed is reaching the end of its useful life. For all of the above tests, the probe was placed in the last 0.6 cm of a 10 cm bed, so the location of the probe can be adjusted to a higher location in the bed to give a warning as to when the bed will become saturated. This methodology is especially useful if multiple probes are placed in the bed, as this will allow the expected shape and magnitude of the peak to be identified from the probes located at higher positions in the bed and compared to the results from the later probes which will indicate that it is time for the bed to be regenerated or changed.

Example 2

Figure 8:
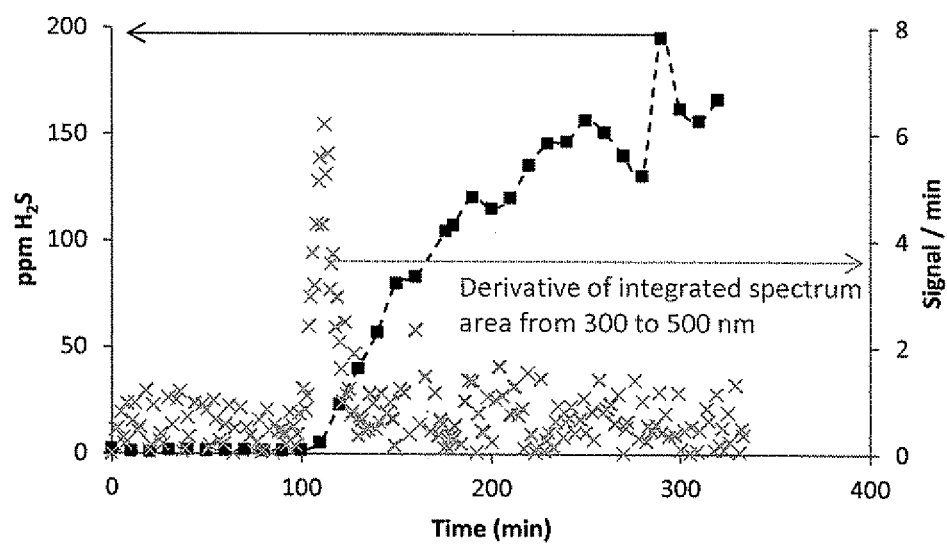
FIG. 8 is a spectrum showing $H_2S$ breakthrough and derivative of integrated UV-Vis spectrum area from 300 nm to 500 nm versus time for an adsorption test with a feed of 162 ppm $H_2S$ in $H_2$ at a face velocity of 10 cm/s and a residence time of 0.5 seconds.
Figure 9:
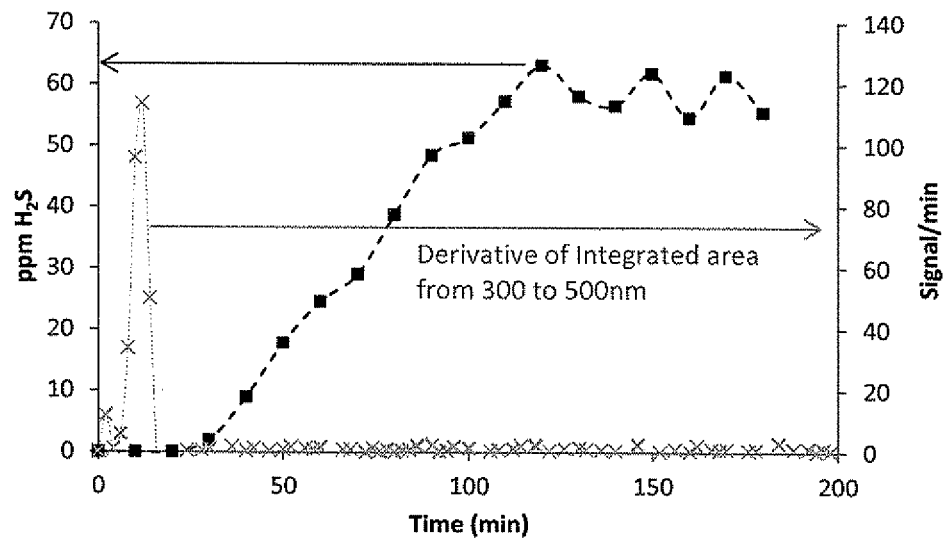
FIG. 9 is a spectrum showing $H_2S$ breakthrough and derivative of integrated UV-Vis spectrum area from 300 nm to 500 nm versus time for an adsorption test with a feed of 63 ppm $H_2S$ in $H_2$ at a face velocity of 10 cm/s and a residence time of 0.1 seconds.

Predicting Breakthrough on CuZn Supported on SiO$_2$ at Lower H$_2$S Concentrations The above results show that UV-Vis spectroscopy can be used to identify the saturation of a CuZn/SiO$_2$ adsorbent bed during the removal of H$_2$S. These experiments, however, were conducted at a high concentration (870 ppm) of H$_2$S while the sorbent bed will likely be used at lower concentrations. The first experiment at lower concentration was conducted with a feed of 162 ppm H$_2$S in H$_2$, and the probe was placed in the last 0.6 cm of the 5 cm bed. The H$_2$S breakthrough curve and derivative of the integrated spectral area are shown in FIG. 8. As with the test conducted at 870 ppm, the UV-Vis sensing method was able to predict H$_2$S breakthrough as indicated by the maximum of the spectral area derivative at the breakthrough point. A similar result was obtained for the test conducted with an inlet H$_2$S concentration of 63 ppm (FIG. 9). During this test, the maximum of the UV-Vis signal derivative curve occurred about 10 minutes before breakthrough; however, this could be due to the probe not being properly positioned at the bottom of the bed. In this case the bed length was only 1 cm long with the probe occupying 0.6 cm of this length.

Example 3

Figure 10:
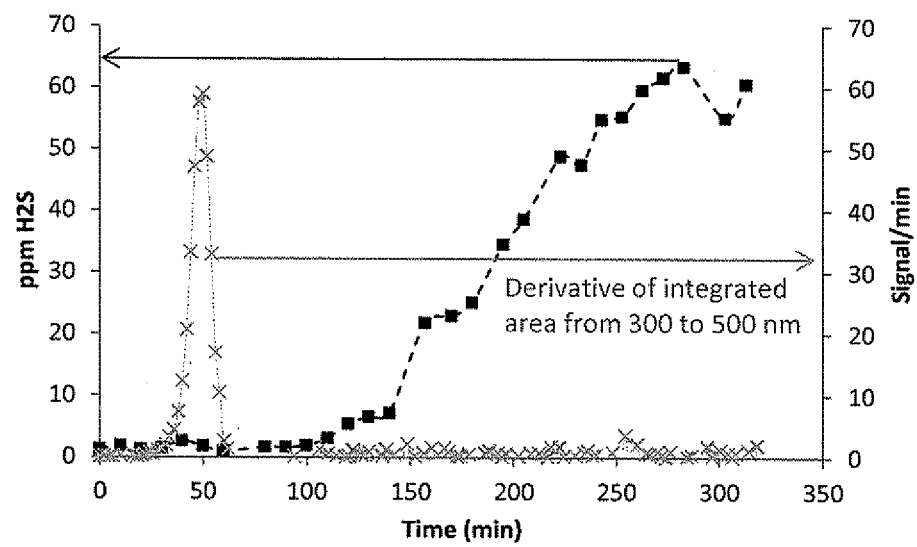
FIG. 10 is a spectrum showing $H_2S$ breakthrough and derivative of integrated UV-Vis spectrum area from 300 run to 500 nm versus time for an adsorption test with a feed of 63 ppm $H_2S$ and 20% $CO_2$ with a balance of $H_2$ at a face velocity of 10 cm/s and a residence time of 0.2 seconds.
Figure 11:
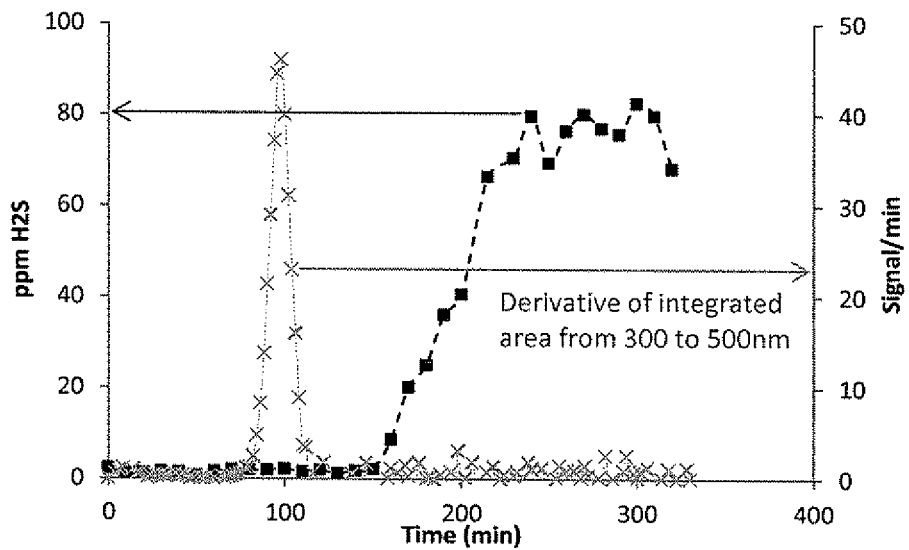
FIG. 11 is a spectrum showing $H_2S$ breakthrough and derivative of integrated UV-Vis spectrum area from 300 nm to 500 nm versus time for an adsorption test with a feed of 83 ppm $H_2S$ and 20% $CO_2$ with a balance of $H_2$ at 50% relative humidity, a face velocity of 10 cm/s, and a residence time of 0.15 seconds.

Predicting Breakthrough on CuZn Supported on SiO$_2$ in the Presence of CO$_2$, Moisture, and CO The previous data showed that breakthrough could be predicted in the absence of any competing species that could induce a surface chemistry change such as CO$_2$, CO, and moisture. The presence of 20% CO$_2$ and 20% CO$_2$ at 50% relative humidity did not have an impact on the ability of the derivative of the integrated spectrum area to predict breakthrough (FIGS. 10 and 11). For both of these tests spectral changes significant enough to impact the sensing method were not observed. The presence of CO$_2$ in the feed resulted in the formation of a small peak centered below 300 nm. The magnitude of this peak was significantly less than the peak resulting from the sulfidation of the sorbent.

Figure 12:
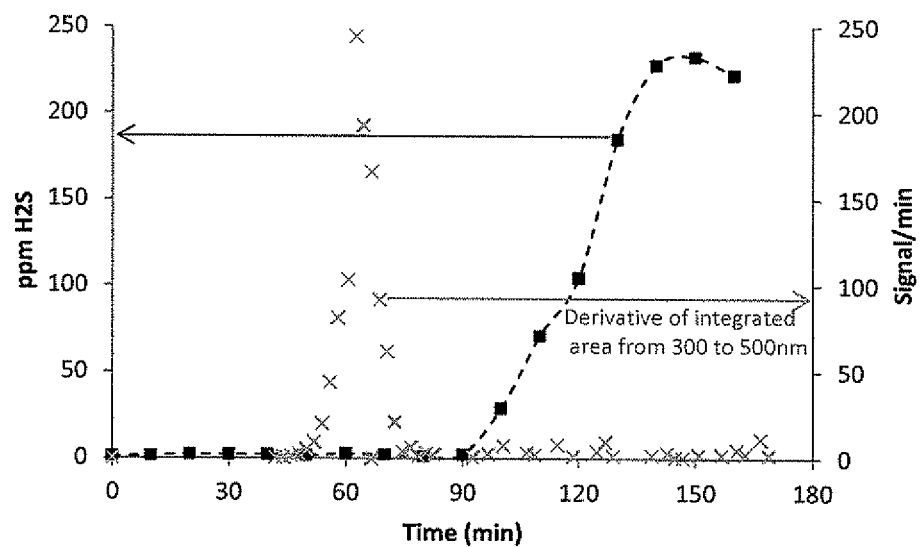
FIG. 12 is a graph showing $H_2S$ breakthrough and derivative of integrated UV-Vis spectrum area from 300 nm to 500 nm versus time for an adsorption test with a feed of 250 ppm $H_2S$, 20% $CO_2$, 20% CO, 20% $N_2$ with a balance of $H_2$ at 50% relative humidity, a face velocity of 10 cm/s, and a residence time of 0.15 seconds.

The final test to screen whether the presence of other components impact the ability of the method to sense breakthrough was conducted with an atmosphere containing 250 ppm H$_2$S, 20% CO$_2$, 20% CO, 20% N$_2$, and a balance of H$_2$ (FIG. 12). The maximum of the derivative for the integrated UV-Vis Signal was observed 30 minutes before breakthrough occurred.

We claim:

1. A method for determining the degree of saturation or deactivation of an adsorbent bed or a catalyst bed in a commercial scale reactor, wherein the adsorbent or catalyst is in contact with one or more species to be adsorbed, the method comprising:
   (a) measuring electromagnetic radiation reflected from the adsorbent bed or the catalyst bed using a sensor at a single, fixed location within the adsorbent bed or the catalyst bed, wherein step (a) is repeated and the sensor is at the single, fixed location,
   (b) taking a derivative of a spectroscopic property of the electromagnetic radiation at a single wavelength or, at multiple wavelengths, as a function of time, wherein all data for the spectroscopic property are measured at the single, fixed location,
   (c) determining the degree of saturation or deactivation of the adsorbent bed or the catalyst bed at a given time prior to saturation or deactivation of the adsorbent bed or the catalyst bed, and
   (d) changing or regenerating the adsorbent bed or the catalyst bed depending on the degree of saturation or deactivation of the adsorbent bed or the catalyst bed.

2. The method of claim 1, wherein the reflected electromagnetic radiation is measured using UV-Vis spectroscopy.

3. The method of claim 1, wherein the reflected electromagnetic radiation is measured using Raman spectroscopy.

4. The method of claim 1, wherein the reflected electromagnetic radiation is measured using Infrared spectroscopy.

5. The method of claim 1, wherein the single, fixed location is at the bottom of the adsorbent bed or the catalyst bed.

6. The method of claim 1, wherein the adsorbent bed or the catalyst bed changes color in response to the adsorption of the one or more species, wherein the color change corresponds to a specific wave number and frequency reflected from the adsorbent bed or the catalyst bed.

7. The method of claim 1, wherein breakthrough of the adsorbent bed or the catalyst bed is determined by the maximum of absolute value of the first-order derivative of the spectroscopic property or zero of the second-order derivative.

8. The method of claim 7, wherein the spectroscopic property is a raw signal, Kubelka Munk function, processed signal, or a combination thereof.

9. The method of claim 8, wherein the processed signal is selected from the group consisting of reflectance, absorbance, transmission, and combinations thereof.

10. The method of claim 9, wherein the processed signal includes mathematic equation transformed raw data.

11. The method of claim 1, wherein the one or more species to be adsorbed to the adsorbent bed or the catalyst bed is hydrogen sulfide.

12. The method of claim 11, wherein the hydrogen sulfide is a contaminant in a gaseous fuel stream.

13. The method of claim 11, wherein the spectroscopic property is a processed signal, and wherein the processed signal is reflectance, wherein the degree of saturation of the adsorbent bed or the catalyst bed corresponds with when a spectrum of the reflectance versus time has a peak in the range of 250 nm to 500 nm.

14. The method of claim 13, wherein the peak is at about 350 nm.

15. The method of claim 11, wherein the concentration of the hydrogen sulfide to be adsorbed is less than 1000 ppm.

16. The method of claim 1, wherein the degree of saturation of the adsorbent bed or the catalyst bed can be determined in the presence of competing species that can induce a change in surface chemistry of the adsorbent bed or the catalyst bed.

17. The method of claim 16, wherein the one or more species to be adsorbed is hydrogen sulfide and the competing species are selected from the group consisting of carbon dioxide, carbon monoxide, moisture, and nitrogen, and combinations thereof.

18. The method of claim 1, wherein the adsorbent bed or catalyst bed is selected from the group consisting of zinc oxide (ZnO), supported zinc oxide, iron oxides, supported iron oxides, copper oxides, supported copper oxides, and zeolites, and combinations thereof.

19. The method of claim 1, wherein the sensor is stationary.

20. The method of claim 1, wherein the degree of saturation or deactivation of the adsorbent bed or the catalyst bed is determined by analyzing the derivative of the spectroscopic property of the electromagnetic radiation collected from the single, fixed location.

\* \* \* \* \*